United States Patent [19]

Zewert et al.

[11] Patent Number: 5,290,411
[45] Date of Patent: Mar. 1, 1994

[54] ACRYLIC POLYMER ELECTROPHORESIS SUPPORT MEDIA

[75] Inventors: Thomas Zewert, Pasadena; Michael G. Harrington, La Canada, both of Calif.

[73] Assignee: California Institute of Technology, Pasadena, Calif.

[21] Appl. No.: 74,266

[22] Filed: Jun. 9, 1993

Related U.S. Application Data

[63] Continuation of Ser. No. 913,234, Jul. 14, 1992, abandoned.

[51] Int. Cl.$^5$ .......................... C25B 1/00; C08F 18/00
[52] U.S. Cl. .............................. 204/128.8; 526/320; 526/934; 436/516
[58] Field of Search ............................ 526/320, 934; 204/182.8, 299 R; 436/516

[56] References Cited

U.S. PATENT DOCUMENTS

| | | | |
|---|---|---|---|
| 2,129,722 | 9/1938 | Woodhouse | 526/320 |
| 2,484,487 | 10/1949 | Caldwell | 526/320 |
| 3,554,747 | 1/1971 | Dastoor | 526/934 |
| 3,741,923 | 6/1973 | Fritsche et al. | 525/214 |
| 4,006,069 | 2/1977 | Hiratsuka et al. | |
| 4,146,454 | 3/1979 | Haber | 436/516 |
| 4,148,869 | 4/1979 | Deaton | 436/516 |
| 4,277,582 | 7/1981 | Mueller et al. | 526/320 |
| 4,305,798 | 12/1981 | Cunningham et al. | 436/516 |
| 4,321,349 | 3/1982 | Rich | 526/320 |
| 4,337,189 | 6/1982 | Bromley et al. | 526/320 |
| 4,429,097 | 1/1984 | Chang et al. | 526/320 |
| 4,431,498 | 2/1984 | Hickner | 526/320 |
| 4,777,230 | 10/1988 | Kamath | 526/320 |
| 4,883,659 | 11/1989 | Goodman et al. | 526/320 |
| 4,931,522 | 6/1990 | Catena | 526/320 |
| 4,978,777 | 12/1990 | Takagawa et al. | 526/320 |
| 5,055,517 | 10/1991 | Shorr et al. | |
| 5,086,143 | 2/1992 | Sutton et al. | 526/320 |

FOREIGN PATENT DOCUMENTS

| | | | |
|---|---|---|---|
| 0113700 | 7/1984 | European Pat. Off. | 204/182.8 |
| 0163472 | 12/1985 | European Pat. Off. | 204/182.8 |
| 2445409 | 4/1976 | Fed. Rep. of Germany | 204/299 R |
| 60-147419 | 8/1985 | Japan | 526/320 |

OTHER PUBLICATIONS

"Polyethylene glycol derivatives of base and sequence specific DNA ligands": Nucleic Acids Research vol. 9 No. 1 1981 pp. 95-119.

"Fractionation of Linear Polyethylene with gel permeation chromatography" Advances in Chemistry Series 125 ACS Washington D.C. (1973) Nakajima pp. 98-107.

Encyclopedia of Polymer Science and Engineering, vol. 5, Dielectric Heating to Embedding, John Wiley & Sons.

*Primary Examiner*—Joseph L. Schofer
*Assistant Examiner*—N. Sarofim
*Attorney, Agent, or Firm*—Poms, Smith, Lande & Rose

[57] ABSTRACT

Electrophoresis support media which include one or more polymers made from hydroxy alkyl esters of acrylic or methylacrylic acid or poly (alkylene glycol) esters of acrylic or methacrylic acid. These acrylic or methacrylic monomers are polymerized or copolymerized to form electrophoresis support media which can be used in place of polyacrylamide gels, agar gels and agarose gels. The acrylic or methacrylic ester monomers may be cross-linked with various cross-linking agents to provide electrophoresis support media with a wide range of pore sizes and physical strength. The electrophoresis support media is well-suited for use with organic solvents.

14 Claims, No Drawings

ACRYLIC POLYMER ELECTROPHORESIS SUPPORT MEDIA

This is a continuation of copending application(s) Ser. No. 07/913,234 filed on Jul. 14, 1992 now abn.

BACKGROUND OF THE INVENTION

The present invention was made with the support of the National Science Foundation Grant No. DIR-8809710. The United States Government may have rights to the invention.

1. Field of the Invention

The present invention relates generally to the support mediums used in electrophoresis. More particularly, the present invention is directed to the use of polymers and copolymers which include hydroxyalkyl esters of acrylic or methacrylic acid or poly(alkylene glycol) esters of methacrylic or acrylic acid as at least part of the support media.

2. Description of Related Art

Support media are commonly used in electrophoresis systems to suppress convection caused by gravity, thermal gradients or concentration gradients. The support media which have been used conventionally include powdered and porous solids, fibrous materials and gels. The powdered and porous materials which are used as electrophoresis media includes cellulose, starch, silica, glass, polyurethane foam and glass powder. For the most part, the powdered and porous solid electrophoresis media have been replaced by gels which have a higher resolving power. The powdered and porous solids are generally reserved for large scale preparative separations.

Fibrous materials, such as paper have been used in electrophoresis for many years. Paper electrophoresis support media became popular due to their low cost and ease of handling. However, the use of paper as a support media has largely been replaced with gels due to problems experienced with variations in different batches of paper and impurities in the paper which caused undesirable and unpredictable absorptive properties.

Cellulose acetate membranes have also been used as an electrophoresis support media. Cellulose acetate membranes do not have the undesirable absorptive properties of paper and have a uniform microporous structure and are chemically inert. However, cellulose acetate must be laminated to a flexible plastic support due to the inherent brittleness of dry cellulose acetate.

The most popular electrophoresis support materials are based on molecular-sieve gels. Starch gels were initially used in the early 1950's for the separation of proteins. However, the narrow range of porosities and the fragile nature of starch gels have rendered them obsolete. Agar and agarose gels have been widely used as an electrophoresis support media. Agar and agarose gels are obtained from polysaccharides extracted from red algae. Agar and agarose gels have not been widely used (except for large DNA molecules) as an electrophoresis support media because of limited sieving properties and a high content of anionic residues, such as sulfate and pyruvate.

Polyacrylamide gel (PAG) has been widely adopted as the support media of choice for the separation of both proteins and DNA. Cross-linked polyacrylamide provides good resolution in many applications because it possesses sieving as well as anti-convective properties. The sieving properties of cross-linked polyacrylamide gels are particularly well-suited for molecular weight separations. By varying the percentage of monomer or cross-linker, the nature of the gel can be changed to suit a variety of separations from small (1,000 kD) peptides to large (500,000 kD) proteins.

Despite the numerous advantages and popularity of polyacrylamide gel support media, there are a number of inconveniences, hazards and limitations which accompany the use of this material. For example, the acrylamide monomer and the bis-acrylamide cross-linker represent a serious health hazard. Although the polymer is not toxic, exposure to the monomer and cross-linker during preparation of the gel poses significant health concerns. In addition, residual and derivative chemicals present during post-electrophoresis processing also pose health concerns.

The health problems associated with acrylamide monomer are compounded by the fact that the toxic effects of acrylamide are cumulative. The toxicity problem associated with acrylamide monomers can be carefully controlled in a research setting. However, toxicity concerns may limit the use of polyacrylamide gel in clinical laboratory settings where people being exposed to the toxins may not be well-informed about the risks associated with polyacrylamide monomer and carefully trained with respect to proper handling procedures.

Another problem associated with polyacrylamide gel support media is the difficulty in forming gels of reproducible properties. Acrylamide monomers and the bis-acrylamide cross-linkers are commercially available as extremely pure and uniform compositions. However, separation of the electrophoresis support media involves a high degree of skill and care. Slight changes in preparation technique from batch to batch results in the formation of gels having slightly different properties. Further, the pouring process for preparation of the gel is prone to minor variations which result in the formation of gels which vary in composition at different locations within the gel.

The variability present in polyacrylamide gel support media results in inconsistent protein migration within a particular gel media. Further, protein migration is not reproducible when different batches of gel are used. As a result of these inconsistencies, polyacrylamide gel support media has not been widely used in clinical applications. Instead, cellulose acetate membranes have been used even though they have considerably less resolution power.

Two dimensional electrophoresis (2DE) is a technique which allows the identification of thousands of molecules simultaneously. In 2DE systems, the samples are subjected to electrophoresis based on two independent variables such as charge and mass. For example, in a first dimension, isoelectric focusing (IEF) is used to separate complex mixtures based on charge. In a second dimension, polyacrylamide gel electrophoresis is used to separate the samples based on mass. The resulting 2-dimensional image contains the positional coordinates and quantity of each species as well as all interconnecting correlations. Unlike a series of one-dimensional separations, the 2DE gel image provides a data base which is suitable for determining individual differences between samples and for the analysis of molecular networks.

The full potential of two-dimensional electrophoresis has been difficult to obtain because of non-uniformities in the polyacrylamide gel support media. For example, the computer matching of up to thousands of protein spots on a two-dimensional electrophoresis is greatly hindered by artifacts in the polyacrylamide gel support media such as bubbles, insoluble material, polymer concentration gradients and cross-link density variabilities. These variabilities or artifacts in the gel give rise to glitches in protein spot structure and gel-to-gel variations in composition that result in irreproducibility of relative protein or DNA migration velocities.

In view of the above problems with present electrophoresis support media, it would be desirable to provide improved support media which overcome the disadvantages set forth above. For example, it would be desirable to provide electrophoresis support media which are non-toxic and easily handled. Further, the procedures and techniques for forming the support media should be simple and easily mastered so that uniform support media with reproducible characteristics can be prepared routinely. Finally, the properties of the support media must be such that they are suitable for use in high performance electrophoresis systems, such as two-dimensional electrophoresis.

Many times it is desirable to use organic solvents in the electrophoresis process. The present electrophoresis medias, such as polyacrylamide gel are not well-suited for use with organic solvents to separate hydrophobic molecules. Accordingly, there is also a need to provide electrophoresis support media which not only have all of the above mentioned desired characteristics, but are also suitable for use with organic solvents.

SUMMARY OF THE INVENTION

In accordance with the present invention, electrophoresis support media are provided which overcome many of the above-mentioned problems associated with existing support media. The electrophoresis support media of the present invention are non-toxic, inert and particularly well-suited for use in high performance electrophoresis, such as two-dimensional electrophoresis. The media are relatively simple to prepare utilizing conventional polymerization procedures and result in the formation of support media having uniform characteristics which are reproducible.

The present invention is based upon the discovery that hydroxyalkyl esters of acrylic or methacrylic acid or poly(alkylene glycol) esters of methacrylic or acrylic acid may be used alone or in combination with polyacrylamide gel as an electrophoresis support media.

As a feature of the present invention, monomers such as poly(ethylene glycol) acrylate, poly(propylene glycol) acrylate, glycerol acrylate, hydroxyalkyl acrylate, poly(ethylene glycol) methacrylate, poly(propylene glycol) methacrylate, glycerol methacrylate and hydroxyalkyl methacrylates may be used to form polymers that are especially well-suited for use as electrophoresis support media.

The alkylene glycol esters of methyacrylic or acrylic acid in accordance with the present invention may be polymerized and cross-linked to different degrees to provide electrophoresis support media ranging from viscous liquids to gels. As a result, a wide range of electrophoresis separation media can be prepared which have a wide range of desired separation characteristics.

The electrophoresis support media polymers in accordance with the present invention avoid the problems associated with gels made from naturally occurring materials, such as agarose and agar, and also avoids many of the problems associated with polyacrylamide gels. Accordingly, the electrophoresis support media of the present invention will not only be useful for high performance electrophoresis, but will also be useful in a wide variety of settings where a stable, uniform and reproducible electrophoresis is required.

The above-discussed and many other features and attendant advantages of the present invention will become better understood by reference to the following detailed description.

DETAILED DESCRIPTION OF THE PREFERRED EMBODIMENTS the use of
The present invention involves hydroxyalkyl esters of acrylic or methacrylic acid or poly(alkylene glycol) esters of methacrylic or acrylic acid as an electrophoresis support media. The various support media encompassed by the present invention may be used in a wide variety of electrophoresis systems as a substitute for cellulose acetate, agarose gel, agar gel, polyacrylamide gel or other conventional support media. The support medias encompassed by the present invention can be formed into slabs, columns, or any of the other well-known shapes typically employed in gel electrophoresis systems ranging from capillary zone electrophoresis to industrial scale electrophoresis.

The electrophoresis support media of the present invention is composed of one or more polymers which are made from poly(alkylene glycol) esters of methacrylic or acrylic acid. Suitable monomers include poly(ethylene glycol) acrylate, poly(propylene glycol) acrylate, glycerol acrylate, hydroxyalkyl acrylate, poly(ethylene glycol) methacrylate, poly(propylene glycol) methacrylate, glycerol methacrylate, hydroxyalkyl methacrylate and derivatives thereof. With respect to poly(ethylene glycol) acrylate or methacrylate, the monomer should have from 1 to 100 repeat units in the poly(ethylene glycol) and preferably the monomer will have from 4 to 8 repeat units in the poly(ethylene glycol). With respect to the poly(propylene glycol) acrylate or methacrylate, the monomer should have from 1 to 100 repeat units in the poly(propylene glycol) with monomers having 8 repeat units in the poly(propylene glycol) being preferred. The hydroxyalkyl acrylate or methacrylate monomer should have hydroxyalkyl groups having from 1 to 10 carbon atoms with hydroxyalkyl groups having from 2 to 4 carbon atoms being preferred.

The monomers of the present invention are polymerized according to well-known polymerization techniques for polymerizing acrylates and methacrylates. Such procedures typically involve the addition of a radical initiator, such as ammonium persulfate (APS) or tetramethylene ethylenediamine (TEMED). As is well known, the temperature at which polymerization of acrylic or methacrylic esters or alcohols is conducted must be carefully controlled to provide reasonably rapid polymerization without generating excess heat.

The degree of polymerization may be varied widely depending upon the type of sample being separated and the desired result. Polymerization of the monomers can be terminated in accordance with well known procedures to provide support media ranging from viscous solutions to gels. Molecular weight ranges for the polymers will normally vary from 100,000 to 5,000,000. The monomers may be polymerized by solution polymerization, bulk polymerization or any of the other conventional polymerization processes. Solution polymerization is preferred. The support media of the present invention may be used to form electrophoresis gel slabs which vary in size from 1×1 centimeter up to 40×40 centimeters. The thickness of the gel slab can vary from relatively thin gels having a thickness of 0.1 mm up to relatively thick gels having thicknesses on the order of 1.0 cm. The gels may be formed into columns ranging in length from 1 cm to 100 cm and having diameters on the order of 0.01 mm to 10 cm.

The viscosity of the electrophoresis media in accordance with the present invention may be controlled to provide media ranging from viscous solutions to medium or high density gels. The viscosity of the solutions is controlled by the cross-link density of the polymer. When media in the form of viscous solutions are desired, the cross-link density is preferably between about 0 and 1 %. For medium to high density gels, the cross-link density may range from 0 to 25 %

Any of the above mentioned polymers may be used alone or in combination to form a homopolymer or copolymer which may be used as an electrophoresis support material. In addition, cross-linking agents may be used to control viscosity of the media, increase the strength of the gel and provide another means for modifying the gel to provide different levels of sample migration inhibition. Suitable cross-linking agents include tetraethyleneglycol acrylate, tetraethyleneglycol methacrylate, pentaerythritol dimethacrylate, polyethyleneglycol diacrylate, polyethyleneglycol dimethacrylate, bisacrylamide and piperazine diacrylate.

The cross-linking agents are added and copolymerized with the above-mentioned monomers in accordance with conventional acrylate/methacrylate polymerization procedures. The amount of cross-linking agent used in any particular electrophoresis support media can be varied widely depending upon the desired level of sample migration inhibition. The amount of cross-linking agent added can range from 0 mole percent to 50 mole percent of monomer. Preferably, the amount of cross-linking agent added will not exceed 10 mole percent for most applications.

If desired, the monomers in accordance with the present invention may be copolymerized with acrylamide. The copolymerizations will be between random and alternate with respect to monomer incorporation into the polyacrylamide as determined by published calculations using reactivity ratios of the monomers (T. E. Zewert and M. G. Harrington, Electrophoresis, In Press, 1992). As a result, the final gel will be molecularly homogeneous.

Acrylamide can be copolymerized with the monomers of the present invention in any mole percent desired, however, it is preferred, with respect to hydroxy esters of acrylic and methacrylic acid, that the amount of acrylamide in the final gel be less than 70 weight percent.

The porosity of the support media in accordance with the present invention may be varied widely depending upon the particular monomer, degree of polymerization, particular cross-linking agent, if any, and the degree of cross-linking. The differential migration velocity of a given protein is recognized as an indication of media porosity. To achieve desired pore sizes, the above listed parameters may be varied until the desired differential migration velocity of a particular protein is obtained.

The monomers of the present invention are used in the same manner as acrylamide monomer to form gel slabs or columns. The preparation of electrophoresis support media is described in detail in a number of references including: ELECTROPHORESIS—Theory, Methods, and Applications, Vol. 2, edited by Milan Bier (Academic Press, 1967); 2) GEL ELECTROPHORESIS OF PROTEINS, edited by Michael J. Dunn (Wright Bristol, 1986); 3) The Practice of Quantitative Gel Electrophoresis by Andreas Chrambach (Advanced Methods in the Biological Sciences, IRL Press Limited, 1982); 4) GEL ELECTROPHORESIS OF NUCLEIC ACIDS—A Practical Approach, edited by D. Rickwood an B. D. Hames (IRL Press, 1990).

The polymer electrophoresis support media made with the above monomers in accordance with the present invention are particularly well-suited for use in two dimensional electrophoresis systems. Such systems are described in detail in "METHODS: A Companion to Methods in Enzymology, Volume 3, No. 2, October, pp. 98-108 1991. The contents of this reference, as well as all of the other cited articles and references disclosed herein, are hereby incorporated by reference.

The electrophoresis support media in accordance with the present invention is well-suited for use with both aqueous and organic electrophoresis solvents. The use of organic solvents in electrophoresis is important for separating hydrophobic materials. Typical organic solvents which can be used in combination with the electrophoresis media include alcohols, dimethyl formamide (DMF), dimethyl sulfoxide (DMSO), tetramethylurea (TMU), formamide, tetramethylene sulfone, chloral hydrate, N-methyl acetamide, N-methyl pyrollidone and phenol. As is well known, a variety of aqueous and organic solvents may be added into the monomer mixture during formation of the electrophoresis gel. For example, the polymerization of polyacrylamide takes place in the presence of a substantially aqueous solvent. When amounts of water miscible solvents such as DMF, DMSO or TMU are added to the acrylamide polymerization mixture, the mechanical strength and clearness of the polymerized gel are severely compromised. The monomers in accordance with the present invention, however, may be polymerized in the presence of organic solvents without adversely affecting the mechanical strength, clearness or other properties required for a suitable electrophoresis support media. Mixed solvents which include high levels of water-miscible organic solvents (i.e. greater than 30 weight percent) may be used.

Examples of practice are as follows:

MATERIALS AND METHODS

Sodium dodecyl sulfate (SDS), ammonium persulfate (APS), piperazine diacrylate (PDA), acrylamide (ACA), bis acrylamide (Bis), tricine, and glycine were all obtained as electrophoresis grade reagents from Bio-Rad Corp. The ethanol used was 200 proof from the Quantum Chemical Corp. (Tuscola, Ill.). Methanol was reagent grade from EM Scientific Corp. (Gibbstown, N.J.). Dimethyl formamide (DMF), dimethyl sulfoxide (DMSO), sulfolane, formamide, hexamethylphoramide (HMPA), tetramethylurea (TMU), 2,2'-azobisisobutyronitrile (AIBN), n-methylpyrrolidinone (NMP), and n-acryloylmorpholine (ACM) were all vacuum distilled after receipt as reagent grade from Aldrich Chemical Company (Milwaukee, Wis.). Low and High molecular weight standards (unstained and prestained) were obtained from Bio-Rad Corp.

Preparation of Monomers

The following monomers (a) and cross-linkers (b) were used as obtained from Monomer-Polymer and Dajak Laboratories, Inc. (Trevost, Penna.); (1a) 2-hydroxyethyl acrylate; (2a) 2-hydroxyethyl methacrylate; (3a) 2-hydroxypropyl acrylate; (4a) 2-hydroxypropyl methacrylate; (5a) 4-hydroxybutyl acrylate; (6a) 4-hydroxybutyl methacrylate; (7a) glycerol monoacrylate; (8a) glycerol monomethacrylate; (9a) poly(ethyleneglycol) monoacrylate 200; (10a) poly(ethyleneglycol) monoacrylate 400; (11a) poly(ethyleneglycol) monomethacrylate (PEGM) 200; (12a) poly(ethyleneglycol) monomethacrylate (PEGM) 400; (13a) poly(propylenglycol) monoacrylate 400; (14a) poly(propylene) monomethacrylate 400; (1b) pentaerythritol dimethacrylate; (2b) glycerol dimethacrylate; (3b) tetraethyleneglycol diacrylate; (4b) tetraethyleneglycol dimethacrylate; (5b) poly(ethyleneglycol) diacrylate 200; (6b) ethyleneglycol dimethacrylate; and (7b) poly(ethyleneglycol) dimethacrylate 1000 Acrylamide and N-acrylolmorpholine were obtained from the same source as the other monomers. The structures of these monomers and cross-linkers are set forth in Tables 1 and 2.

TABLE 1

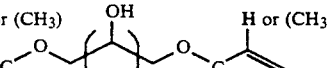

TABLE 2

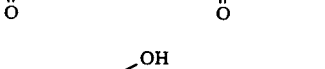

TABLE 2-continued

Crosslinkers

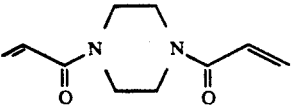

Piperazine diacrylate
PDA 50-100 ppm of the polymerization inhibitors methylhydroquinone and/or hydroquinone were present in the monomers upon receipt. These inhibitors cause color changes in the polymer medias upon polymerization and slowed down polymerization. This problem was overcome by the addition of more catalyst. The catalyst which was used for polymerizations, unless otherwise indicated, was APS with TEMED. The migration properties of the proteins seemed not to be affected by the presence of the inhibitors and their by-products. This observation was confirmed by comparisons with monomers in which the inhibitor had been removed.

Gels ranged from 7-12% T and 0.5-10% C. 11a, ACA and ACM were the three monomers and bisacrylamide and PDA were the cross-linkers. A ratio of 10:1 (v/v) of 10% (w/v) APS: TEMED was used as catalyst for the polymerizations. The total amount of catalyst used varied with the comonomer ratio, % T, and % C of the gels. For instance, 200 ul APS and 20 ul TEMED were used to polymerize a 10% T and 3% C, 11 ml solution of % 50 PEGM 200% 50 ACA in % 50(v/v) DMF. The particular polymerization was firm gel after 20 min., but was allowed to react for 3 hours to ensure maximal polymerization before the electrophoresis run. Half as much catalyst was added when a totally aqueous solvent with these monomers was used and half again was added when pure ACA was polymerized in water. Polymerization times were kept constant. Gradient gels were poured using a standard two-well gradient maker with two stock solutions. Sucrose was not used when gradients of 11a with ACA were made because the density difference of the monomer solutions was sufficient to pour and maintain a stable gradient.

A dual minigel apparatus with a 300 ml run buffer reservoir was used. An acrylic apparatus was used when solvent was only present in the gel and loading buffer; however, when solvent was present in the run buffer, a polytetrafluoroethylene apparatus was used. Gel size was 1.5×90×70 mm. Five wellcombs were used with the dimension of each comb being 1.5×12×12 mm. Sample volumes of 5 to 40 microliters were loaded into each well. Gels were typically run with a Bio-Rad 3000 Xi power supply at 150 V (constant voltage). In some experiments, the use of cooled (4 C) run buffer was sufficient to keep two gels from heating above room temperature throughout the gel runs.

Protein detection was accomplished by direct staining (silver or Coomassie) of the gel or by staining (Ponceau S or colloidal soll) of PVDF membrane (Millipore) after protein from the gel had been transblotted to it. Silver staining was the preferred method of detection because of its sensitivity for both aqueous and hydroorganic gels.

The mechanical properties of gels composed of ACA, ACM, and 11a were compared by compression measurements. Gels were polymerized as 10×25×40 mm slabs and then cut to the sample dimension: 10×18×30 mm. The gels were 10% T and 3% C; they were allowed to react for 24 hours after 200 ul 10% APS and 20 ul TEMED had been added. No buffer was used, and solutions were degassed. Polymerizations and subsequent measurements were carried out at room temperature (22°-24° C.).

Pressure was applied to the samples from the crosshead of a dynamometer (Instron Engineering Corporation, Canton, Mass.). A metal spacer connected the bottom of the sample to a 50 lb. load cell on which stress load was registered. All of the samples were compressed at a constant rate of 0.02 inch/minute on the 10 mm dimension. The data was collected at 2 second intervals. Hysteresis measurements were conducted to a maximum compression of 0.12 inch.

The absorbance capacity and characteristics with hydroorganic solvents were measured by swelling experiments. ACA and/or monomer 11a mixtures at 10% T and 3% C were polymerized in centrifuge tubes after being degassed. 200 ul 10% APS and 20 ul TEMED were used for each 10 ml of monomer mixture. No buffer was added to the polymerization solution. 1.5 ml pieces of the gels were cut out after 24 hours polymerization and dried for 48 hours at 40° C. in a dessicated oven. Their weight was stable with respect to further drying at this time. The dried polymer pieces were reequilibrated in different solvents at room temperature until their reswollen weight became stable (usually 12 hours).

Various acrylamide/PEGM 200 (11a) copolymers were synthesized in different proportions and their measured properties in different concentrations of sulfolane are summarized in Table 3. These gels contained no cross-linker.

The monomers (7a, 8a, 11a, and 12a) and cross-linkers (3b, 4b, and 5b) showed the most desirable all around features as separation matrices. However, the other monomers and cross-linkers should also provide acceptable support media for electrophoresis. The preferred monomers were further purified prior to polymerization by vacuum distillation (0.7 Torr.). Monomers 11a (PEGM 200) and 12a (PEGM 400) could not be distilled because they polymerized before boiling. More inhibitor (500 ppm methylhydroquinone) was added in an attempt to prevent this spontaneous polymerization, but these monomers reacted with the methylhydroquinone. Therefore, a combination of Bio-Rad AG 501X8 (20-50 mesh) mixed-bed resin and Aldrich (catalog #, 31, 133-2) inhibitor-removal resin was used for their purification.

Preliminary studies of the kinetics of polymerization for the monomers and opacity of gel as a function of different polymerization solvents were made with a Hitachi U-2000 spectrophotometer. All measurements were made at 23° C. 30 ul 10% ammonium persulfate (APS) and 3 ul tetramethylene ethylenediamine (TEMED) were used to catalyze the polymerization of these 2 ml, 12% T and 3% C samples. The samples were blanked against TEMED solutions of the same concentration and solvent. Quartz spectrophotometer cells were used as DMSO clouded disposable polystyrene cells. Unless indicated otherwise, all percentages listed in these examples are volume percentages.

The mechanical and electrophoretic properties of monomers 1a-14a and cross-linkers 1b-8b were examined in purely aqueous environments. The first property tested was the solubility of the monomers and polymers. Unless stated otherwise, the polymers used in the following examples were synthesized in solution.

Monomers 3a, 8a, 10a, and 12a and cross-linkers 1b-7b are all completely miscible with water in polymerized and unpolymerized forms. 7a is miscible up to 20 volume % monomer after which point the water-monomer solution starts to become cloudy. The polymer of 7a is clear in water at all concentration. Monomers 4a-6a, 9a, 13a, and 14a and cross-linker 8b are not soluble or are only very slightly soluble in both the unpolymerized and polymerized forms. 11a is completely soluble as a monomer only below 8 volume % but is completely soluble as a polymer at all concentrations. Above 8 volume %, the monomer and water mixture is turbid. Monomers 1a and 2a are soluble as monomers but insoluble as polymers when TEMED and ammonium persulfate are used as the initiators. However, when AIBN is used as initiator, the polymer of 2a is soluble in water and can be swelled to approximately double its weight and remain clear. 2a can also be polymerized without solvent and then swelled to twice its original weight with water while remaining clear.

The polymers of monomers 3a, 10a and 11a form clear gels at concentrations above 15% T without cross-linker. Uncrosslinked poly(7a) and poly(8a) form non-deformable gels (without any applied stress aside from gravity) at as low as 5% T. 10% T was the lowest concentration for a rigid gel with the uncrosslinked polymer of 11a and 12a. This is to be contrasted with polyacrylamide which does not form robust gels without cross-linker.

For equivalent % T, 8a gives the strongest (i.e., most mechanically robust) gels followed by 7a, 11a and 12a, in order. The most significant difference in gel strength is between 7a and 11a. The 7a and 8a gels with equal cross-linker are significantly stronger than the corresponding % T polyacrylamide gels. The difference in strength is most pronounced at low % C (i.e. >1%). The 11a and 12a gels equivalent in % T to polyacrylamide have less tensile strength (in comparison with polyacrylamide) about 1% C, approximately equal strength at 1%, and more strength below 1% C. Generally, the rigidity of the gels increases with increasing % T and % C. An exception is that about 25-50% C the gels often lose elasticity and become crumbly; in addition, poly (7a) decreases in tensile strength above 15% T.

Monomers 7a, 8a, 11a, and 12a (4-20% T) were polymerized in water with varying amounts (0.1-50% C) of cross-linkers 1b-8b and found to provide acceptable electrophoresis support media. 7a polymerizes most quickly followed by 8a. 11a and 12a generally take two to three times more time to complete polymerization. It was noted that incorporation of 1b into the gel polymerization mixtures consistently weakens the mechanical strength of the resulting gels. Moreover, 1b and 2b generally increase the cloudiness of the matrices. Cross-linkers 2b-7b increase gel strength with increasing % C up to 25% C. An exception is the gels formed with monomer 11a weaken with increasing proportion of cross-linker 6b in the mixture. The following is a ranking of the effectiveness of each cross-linker in increasing hydrogel strength disregarding the exception just mentioned: 3b>4b>5b>6b>2b>1b. The effect of the cross-linkers is for the most part greatest for monomers 11a and 12a. Except for 1b and 2b, the cross-linkers do not significantly affect the transparency of the gels even at concentrations higher than 50%.

The monomers and cross-linkers were tested for their suitability as electrophoresis media. The pH of buffered and unbuffered solutions do not change after monomer or cross-linker addition. Prestained protein standards (molecular weights 5-100 kD) electrophoretically enter and migrate through gels composed of 8a, 11a, and 12a. 11a gives the fastest migration and most extensive penetration of protein followed by 12a and 8a. Polyacrylamide gels give much faster migration under all conditions tested; however, poly (11a) gives sharper protein banding than polyacrylamide in many cases.

The cross-linker which formed gels having the fastest migrations and the most stable gels after electrophoresis was piperazine diacrylate (PDA); the gels with N,N'-methylene bisacrylamide (Bis) as the cross-linker demonstrated protein migration rates comparable to those with PDA but are less mechanically stable. The migration of proteins is faster in gels of 8a, 11a, and 12a prepared with no cross-linker than with those prepared with Bis or PDA. However, these gels without cross-linker are significantly weakened during the electrophoresis run so that they can not be removed from the gel plates without some (usually extensive) structural damage. Therefore, these particular gels are suitable for use in separating and detecting only pre-stained proteins.

The PDA-crosslinked gels, on the other hand, are reasonably robust and can tolerate either silver or Coomassie staining. Membrane transblotting can be performed with the PDA crosslinked gels although methanol has to be excluded from the transblotting buffer as it excessively swells the gels. Methanol can be used to wet the PVDF membrane, but afterward the membrane needs to be rigorously washed to avoid gel swelling.

Protein travels more slowly through gels with cross-linkers 3b-5b than through the gels with the same % C of Bis or PDA; the gels with cross-linkers 3b-5b are less robust as well. As a group, gels with cross-linkers 3b-5b- have very similar properties. 1b, 2b, 6b, and 7b may be used as cross-linkers, however, the mechanical properties of the resulting gels may not be suitable for many applications.

The gels composed of polymerized 7a, 8a, 11a, and 12a become mechanically weaker during the electrophoresis run. The cause of this effect has not been determined. However, hydrolysis of the (meth)acrylic esters can be ruled out with some certainty because the phenomenon is pH independent. The extent of structural weakening during electrophoresis is much less or absent when organic solvents are used in the gels and is not present in copolymers of these monomers with acrylamide.

The various monomers were also tested for their gel-forming properties in organic solvents. Sulfolane (tetramethylene sulfone) has been used widely for separations of hydrophobic proteins and was chosen as an exemplary solvent. Solution polymerizations (15% T, 0% C) were performed in varying mixtures (10-98%) of sulfolane and water for all of the monomers (1a-14a). 100% sulfolane could not be used as it is a solid at room temperature.

It was found that all of the polymerization mixtures formed progressively weaker gels with increasing sulfolane concentrations. Monomers 1a and 2a did not form usable gels when catalyst was added in sulfolane even if sulfolane concentrations were as low as 10%. At this concentration of sulfolane, the monomer 1a and 2a reaction mixtures gave small, slightly swollen opaque masses of polymer. Whereas, at higher concentrations no gelation occurred. Only cloudy solutions that become less viscous with progressively higher concentrations of sulfolane were observed.

Monomers, 3a-6a polymerize very slowly and to a low degree of completion in sulfolane solutions. Monomers 13a and 14a give very weak, clear gels which do not hold solvent well at 50% sulfolane. Above 50% sulfolane concentration, solutions of progressively decreasing viscosity are observed with these monomers. In contrast, monomers 7a and 8a give strong, clear gels at 70% sulfolane. These gels are much more opaque but nonetheless form rapidly even at sulfolane concentrations as high as 90%. Monomers 9a and 10a, give fully swelled gels which are suitable—both in strength and clarity—for electrophoresis at this concentration. Clear, strong gels also form at 98% sulfolane with these monomers although more than half of the solvent is not stably held by the matrix. Monomers 11a and 12a also give gels which can be used for electrophoresis at 90% sulfolane. However, at this concentration the gels are noticeably cloudy and require over 12 hours to completely polymerize.

Monomer 11a showed the best resolution in aqueous electrophoresis studies and does not have the heterogeneous polyethyleneglycol (PEG) chain lengths of monomer 12a which cause 12a to be a very viscous suspension. Solution polymerizations of monomer 11a can be conducted in many solvents. 10% T gels of 11a suitable for electrophoresis can be formed with DMF, DMSO, HMPA, ethanol, methanol, TMU, sulfolane, formamide, ACM, and NMP up to 70% concentrations of these solvents in water. Gels made with 11a monomer can also be formed in 90% sulfolane and 98% formamide. However, gel formation is almost completely inhibited at 99% formamide.

Cross-linkers were not used in these exemplary polymerizations. It was noted that gel strength increased with greater concentrations of formamide, in contrast to polyacrylamide gels. The tolerance of gels made with monomer 11a to organic solvents increases with cross-linker (PDA or Bis) concentrations between 0 and 5% C. Further, the presence of organic solvents allows the monomer to fully go into solution which is not the case, as previously mentioned, in the fully aqueous system.

In the examples, polymerization proceeded more slowly in the organic solvent systems. For example, for the monomers in general, polymerization in water was completed in approximately one-third the time as in 50 DMSO and one-tenth the time compared to 70% DMSO. Similar differences in polymerization rates were observed for the other solvents mentioned above.

All of the monomers (1a-14a), except 4a-6a, have been shown to copolymerize with acrylamide. Solutions of 5% T acrylamide/5% T monomer have less than one percent residual monomer present after three hours of polymerization. The carbon-carbon double bond stretch was monitored by IR at 1725 cm$^{-1}$ and 1750 cm$^{-1}$ to determine the extent of these reactions. The resulting gels were found to be suitable for electrophoresis.

The preceding examples show that all of the acrylic or methacrylic esters or hydroxyalkyls tested provided gels which could be used as an electrophoresis media. Monomers 1a-3a, 7a, 8a, 10a-12a, and cross-linkers 1b-7b were shown to be compatible with direct polymerization in the presence of aqueous solvent. Further, all of the monomers (except 4a-6a) and cross-linkers tested polymerize in hydroorganic environments. Indeed, 9a and 10a form gels in almost pure organic solvent.

From the examples, it is also apparent that proteins can be electrophoresed through gels composed of 8a, 11a, and 12a with clear electrophoretic banding and resolution. In general, the resolution with these gels is on the same order as polyacrylamide. Gels made from 11a and 12a give sharper banding than polyacrylamide. Moreover, there is the significant advantage of less toxicity with these monomers than with acrylamide. Two possible disadvantages in aqueous environment are: (1) the gels are not as mechanically robust as acrylamide at equivalent % T and (2) the rates of protein migration through the gels are significantly slower than for acrylamide. Increases in cross-linker size do not appear to increase pore size and thus migration velocity. However, the addition of organic solvents to the gel buffer may provide an increase in gel porosity to achieve higher migration rates when desired.

The relatively small pore size of the gels in accordance with the present invention may be advantageous for certain peptide separations where high migration speed is not required. An advantage of the exemplary cross-linkers 1b-8b is, that in contrast to PDA and Bis, they do not increase the turbidity of the gels in high concentrations (>8% C). 1b-8b are therefore suitable for use in applications where a high cross-link density is needed. Bulk (unsolvated) polymerization and subsequent hydration is possible with any of the exemplary methacrylate monomers. This is an option not available with acrylamide. The acrylate monomers polymerize poorly without solvent.

The preceding examples show that, when desired, all monomers (except 4a-6a) can be polymerized in solvent, have the solvent evaporated off, and then have the same or a different solvent added at the convenience of the researcher or clinician. The exemplary polymers are much more elastic than acrylamide when dry. Accordingly, they can be handled more easily without a support in this state. Polymers of monomers 1a-3a are much stronger than polyacrylamide in both the dry and hydrated states. As a result, homopolymers of 1a-3a or copolymers of these monomers with acrylamide or the exemplary other monomers may be used as a strong pre-formed electrophoresis support gel. Such gels have many advantages including time savings, ease of preparation and reproducibility.

As a further example, the properties of electrophoresis support media made from monomer 11a with organic solvents were compared to media made under the same conditions with acrylamide (ACA) or N-acryloylmorpholine (ACM). The mechanical, and electrophoretic properties of the 11a media are superior to the ACA gels because the ACA gels lose their ability to function as convective matrices when the organic solvent concentration is greater than 30%.

As can be seen from the data in Table 3, the gels with the best combination of strength and optical properties in these sulfolane concentrations are not at the extremes of PEGM 200 or ACA concentration but near an equal composition of each (i.e. either 60% ACA/40% PEGM 200 or 40% ACA/ 60% PEGM 200). These gels are sufficiently robust and clear (<0.2 OD at 600 nm) for electrophoresis down to 0% concentrations of sulfolane. A 50% ACA/50% PEGM 200 polymerization mixture was tested in a variety of solvents. Although compression and optical data were not obtained, it was evident that the gels of 50% DMF, DMSO, TMU and HMPA were of similar strength and clearness as the sulfolane gels of the same concentration.

TABLE 3

Physical Properties of PEGM 200(11a)/ACA Gels

| Sample[a,b] | 50% Sulfolane | | 70% Sulfolane | | 90% Sulfolane | |
|---|---|---|---|---|---|---|
| | Strength[c] | Opacity[d] | Strength[c] | Opacity[d] | Strength[c] | Opacity[d] |
| 80% ACA 20% PEGM 200 | 1.3 | 0.9 | 1.7 | 1.9 | No Gel | 5.5 |
| 60% ACA 40% PEGM 200 | 1.9 | 0.2 | 2.5 | 0.2 | 0.7 | 1.5 |
| 40% ACA 60% PEGM 200 | 1.6 | 0.1 | 2.4 | 0.1 | 2.2 | 0.1 |
| 20% ACA 80% PEGM 200 | 1.4 | 0.0 | 1.4 | 0.2 | 1.2 | 0.1 |

[a]Samples are 10% T, 3% C (Piperazine diacrylate).
[b]Stress applied as compression at rate of 0.5 mm/min on smallest dimension of 3.0 × 1.8 × 1.0 cm samples.
[c]Load in lb. needed to compress sample 25%.
[d]Optical density at 600 nm.

Table 4 compares the mechanical and optical properties of poly (ACA), poly (ACM), poly (PEGM 200), poly (11a) gels in a variety of solvents. In water, ACA gels are significantly more rigid than their PEGM 200 and ACM counterparts. ACM is slightly stronger than PEGM 200 but much less clear. In 50% DMSO the properties of the pure ACM and ACA materials deteriorate to the extent that they are no longer rigid gels. They are adhesive and are not able to absorb all the solvent present and also exude large amounts of solvent at the slightest pressure. These materials are also completely opaque. The pure PEGM 200 (11a) gel is somewhat cloudy in 50% DMSO but still maintains its structural integrity and absorbs all of the solvent present. Combining both PEGM 200 (11a) and ACM with ACA separately in equal mixtures causes a synergistic effect where the composite gels are stronger and clearer than those composed of the separate components (homopolymers) in 50% DMSO. Both composite gels are of suitable strength for electrophoresis systems. However, the PEGM 200 (11a) gel is demonstrably superior in mechanical and optical properties. Also, the 50% ACM/50% ACA gel is more adhesive than the 50% PEGM 200/50% ACA gel and tends to exude more solvent upon the application of pressure. There is also a small amount (5% volume) of free solvent after the 50% ACM/50% ACA polymerization; whereas, no free solvent is observed after the 50% PEGM 200/50% ACA polymerization.

TABLE 4

Comparison of Properties of PEGM 200 (11a), ACM; and ACA Gels

| Sample[a,b] | Solvent | Opacity[c] | Strength[d] |
|---|---|---|---|
| ACA | H₂O | 0.0 | 2.8 |
| ACM | H₂O | 3.3 | 1.2 |
| PEGM 200 | H₂O | 0.3 | 0.8 |
| ACA | 50% DMSO/50% H₂O | 48.3 | 0.0 |
| ACM | 50% DMSO/50% H₂O | 39.7 | 0.1 |
| PEGM 200 | 50% DMSO/50% H₂O | 4.1 | 0.5 |
| 50% PEGM 200/ 50% ACA | 50% DMSO/50% H₂O | 0.1 | 2.1 |
| 50% ACM/ 50% ACA | 50% DMSO/50% H₂O | 2.4 | 1.3 |

[a,b,c,d]Same comments apply as in Table 3.

It was determined that the 50% PEGM 200/ACA gel generates a higher stress load at equivalent compression than the 50% ACM/ACA gel. Therefore, an application of a greater force is needed to deform the former gel at this stress rate. The ability of the samples to respond to decompression is approximately equal. This observation indicates that the flexibility and relative encumbrance of the chains of these respective polymers combine in such a way as to provide equal relaxation times of the chains under these conditions. The irreversible deformation for the 50% ACM/50% ACA sample is approximately twice that of the 50% PEGM 200/50% ACA sample. This difference in the amount of permanent deformation is significantly magnified when the samples are taken to higher maximum compressions and stress loads.

Permanent deformation is much greater in the pure ACM samples. For instance, the permanent deformation for the 100% ACM gel in water was 11.3% of maximum compression when maximum compression was 35% of the gel dimension; whereas, the 100% PEGM 200 gel had a permanent deformation of 0.2% of maximum compression for the same parameters. Likewise, the pure ACM gel in 50% DMSO had an irreversible deformation of over 50% at these parameters (only an approximate number could be determined because the sample adhered to the compression plates) while the pure PEGM 200 (11a) gel had a corresponding value of only 7.8%.

Many organic solvents inhibit initiators or cause chain transfer. Both of these factors lower molecular weights and increase polymerization times. To avoid these problems a gel can be prepolymerized (in bulk or in aqueous solution) and then dried (if need be) and reswelled in a solvent of choice.

It was determined that there is a general increase in swelling in organic solvents with increasing concentrations of PEGM 200 in the copolymer gel compositions. The only exception to this positive correlation is seen for the 75% PEGM 200/25% ACA composition which has somewhat less solvent gain than the 50% PEGM 200/50% ACA copolymer in sulfolane, water, and formamide.

Electrophoresis of proteins was performed in a variety of solvents up to 98% concentration including, DMF, DMSO, HMPA, EtOH, MeOH, TMU, sulfolane, formamide, ACM, and NMP. Hydrophilic protein standards were obtained commercially and a set of hydrophobic protein standards which included zein, bacteriorhodopsin, and insulin were also obtained. All of the hydrophobic proteins were soluble in a variety of organic solvents. The first two (zein and bacteriorhodopsin) are not soluble in water.

The electrophoresis was carried out with a Tris pH 8.8 to 8.0 buffer in the gel and the running reservoir. Glycine and SDS were also included in the run buffer. Migration of the hydrophobic and hydrophilic proteins into the pure PEGM 200 gel and the gels composed of copolymers of PEGM 200 and ACA with all of the solvents at 50% concentration was demonstrated.

The 50% PEGM 200/50% ACA copolymer gave satisfactory resolution of the proteins and excellent solvent resistance. As a result, this is a preferred composition. In totally aqueous conditions, this particular gel does not give as good resolution or as much migration of the hydrophilic standard proteins as pure ACA does, especially for higher molecular weight proteins. But in hydroorganic environments (30% sulfolane and 50% formamide), the resolution is comparable to that achieved in pure acrylamide swelled in a totally aqueous buffer. This phenomenon may be due to the fact that a small amount of organic solvent is needed to solvate the polymer chains of the PEGM 200/ACA gels and thus open up their pore structure.

All of the solvents used in this example were compatible with the 50% PEGM 200/50% ACA gel at solvent concentrations greater than 70% so that the gels have sufficient mechanical strength to be transblotted or stained after the run. Some caveats apply to the transblotting and staining procedures. Care has to be taken with gels run with alcohols as solvents as the solvent evaporates quickly if the gels are not covered during polymerization or the run and if the apparatus is not cooled. Further, some bubbles form in the matrix with DMSO during polymerization. Problems with inhomogeneities in band structure can be avoided in this case if the well comb is inserted near the end of polymerization to avoid trapping bubbles. Also, sulfolane has a particularly acrid odor which acts as a cumulative respiratory irritant. This solvent is very difficult to work with even when most manipulations are performed in a fume hood.

The results of the electrophoresis tests show that ACM/ACA gels have less rapid protein migration and poorer resolution. Also, the mechanical strength and optical properties of the PEGM 200 (11a) gels are greater than the ACM/ACA gels. Moreover, the ACM/ACA gels in several instances decline much more in mechanical and optical properties during the run. This effect is especially pronounced in 50% HMPA and NMP where the ACM/ACA gels do not keep their structural integrity throughout the run.

No reproducible differences in the rates of protein migration through the PEGM 200/ACA gels were observed when PDA, BIS, or a combination of the two were used as crosslinkers. Similar results are obtained for acrylamide. This observation held true with PEGM 200 (11a) polymer and copolymer gels in both aqueous and hydroorganic environments. However, the PDA gels of the same % C are slightly stronger than the corresponding Bis gels in both types of media.

With the 50% PEGM 200/50% ACA gels, >9% T gives gels which can readily be stained and manipulated. Gels with lower concentration polymer can be used, but significantly more care is needed in their handling. The more lightly the gels are cross-linked, the greater the swelling is in the methanol-containing solutions used in silver and Coomassie staining. For 10% T gels, 0.5% C gives a suitable degree of strength for all of the electrophoresis procedures while 3% C gives the optimum characteristics in 50% organic environments. Higher % C's give less elastic, crumblier gels. With >15% C the gels shrink significantly upon polymerization. DMF gives the greatest penetration of zein into the gel and the best resolution of the crude mixtures of proteins. DMF is the solvent, of those tested, in which zein is most soluble. Inclusion of organic solvent (>50%) is critical for sample entry. Urea (4.5M) in the protein sample improves resolution of the zein bands in the gel although zein can be run into the gel and separates without urea. Urea in the gel worsens resolution substantially. Also, the inclusion of solvent in the run buffer, which makes the use of a teflon apparatus mandatory, does not improve results.

With Tris, the separations were not significantly affected by ionic strength over variations from 50 to 400 mM. The pH of the Tris solution is a factor. However, as the pH is lowered, greater penetration of zein and hydrophilic proteins is observed. This effect was seen in both 50% DMF and DMSO and seems to level off at pH 8.0.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. An electrophoresis support media comprising a polymer gel which is made from monomers selected from the group consisting of poly(alkylene glycol) esters of methacrylic acid and poly(alkylene glycol) esters of acrylic acid, said polymer gel being in the shape of a slab or column said polymer gel slab or column comprising at least one will into which samples are loaded.

2. An electrophoresis support media according to claim 1 wherein said polymer gel is made from a monomer selected from the group consisting of poly(ethyleneglycol) acrylate, poly(propyleneglycol) acrylate, poly(ethyleneglycol) methacrylate, and poly(propyleneglycol) methacrylate.

3. An electrophoresis support media according to claim 2 wherein said polymer gel is made from a poly(ethyleneglycol) acrylate or methacrylate monomer having from 1 to 100 repeat units in the poly(ethylene glycol).

4. An electrophoresis support media according to claim 2 wherein said polymer gel is made from a poly(propyleneglycol) acrylate or methacrylate monomer having from 1 to 100 repeat units in the poly(propyleneglycol).

5. An electrophoresis support media according to claim 1 which further includes a cross-linking agent selected from the group consisting of tetraethyleneglycol acrylate, tetraethyleneglycol methacrylate, pentaerythritol di(methacrylate), poly(ethyleneglycol) diacrylate, polyethyleneglycol dimethacrylate, bisacrylamide and piperazine diacrylate.

6. An electrophoresis support media according to claim 2 wherein said media consists essentially of a single polymer.

7. An electrophoresis support media according to claim 7 wherein said monomer from which said polymer is made is poly(ethyleneglycol) methacrylate.

8. An electrophoresis support media according to claim 1 wherein said media further comprises acrylamide monomer copolymerized with said monomer to form a copolymer support media.

9. An electrophoresis support media according to claim 9 wherein said monomer is polyethyleneglycol methacrylate.

10. An electrophoresis support media according to claim 1 which further comprises an electrophoresis solvent dispersed within said support media.

11. An electrophoresis support media according to claim 10 wherein said electrophoresis solvent comprises an organic solvent.

12. An electrophoresis support media according to claim 1 wherein said polymer gel is in the shape of a slab.

13. An electrophoresis support media according to claim 1 wherein said polymer gel is in the shape of a column.

14. An electrophoresis support media according to claim 1 wherein said well includes a sample located therein.

* * * * *